(12) United States Patent
Nishide et al.

(10) Patent No.: US 7,508,903 B2
(45) Date of Patent: Mar. 24, 2009

(54) COLLIMATOR CONTROL METHOD AND X-RAY CT APPARATUS

(75) Inventors: Akihiko Nishide, Tokyo (JP); Masatake Nukui, Tokyo (JP); Katsumi Azu, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 240 days.

(21) Appl. No.: 11/199,429

(22) Filed: Aug. 8, 2005

(65) Prior Publication Data

US 2006/0039536 A1 Feb. 23, 2006

(30) Foreign Application Priority Data

Aug. 13, 2004 (JP) ............................. 2004-235899

(51) Int. Cl.
*G01N 23/083* (2006.01)
*G21K 1/04* (2006.01)

(52) U.S. Cl. ..................................... 378/15; 378/151

(58) Field of Classification Search .................. 378/4, 378/15, 19, 151
See application file for complete search history.

(56) References Cited

U.S. PATENT DOCUMENTS

| | | | | |
|---|---|---|---|---|
| 5,386,446 A * | 1/1995 | Fujimoto et al. | ............... | 378/20 |
| 5,684,855 A | 11/1997 | Aradate et al. | | |
| 5,864,598 A | 1/1999 | Hsieh et al. | | |
| 6,023,494 A | 2/2000 | Senzig et al. | | |
| 6,118,839 A * | 9/2000 | Dafni et al. | ................... | 378/15 |
| 6,320,929 B1 * | 11/2001 | Von Der Haar | ................ | 378/4 |
| 6,370,218 B1 * | 4/2002 | Toth et al. | ..................... | 378/19 |
| 6,445,764 B2 * | 9/2002 | Gohno et al. | ................. | 378/19 |
| 6,501,820 B2 * | 12/2002 | Guendel | ..................... | 378/15 |
| 7,076,019 B2 * | 7/2006 | Hagiwara et al. | ............. | 378/16 |
| 7,242,749 B2 * | 7/2007 | Hsieh et al. | ................. | 378/150 |
| 2003/0031290 A1 | 2/2003 | Sugihara et al. | | |
| 2003/0076920 A1 | 4/2003 | Shinno et al. | | |

FOREIGN PATENT DOCUMENTS

| | | |
|---|---|---|
| JP | 06296604 | 10/1994 |
| JP | 2001112747 | 4/2001 |
| JP | 2001145621 | 5/2001 |
| JP | 2002-355242 | 12/2002 |
| JP | 2003-052684 | 2/2003 |
| JP | 2003-159244 | 6/2003 |
| JP | 2003-334188 | 11/2003 |
| JP | 2004-041674 | 2/2004 |
| JP | 2004-041675 | 2/2004 |
| JP | 2004-073360 | 3/2004 |

OTHER PUBLICATIONS

Xiaodong Xu et al.; "Collimator, X-Ray Irradiator, and X-Ray Apparatus"; U.S. Appl. No. 10/982,114; filed Nov. 4, 2004.

* cited by examiner

*Primary Examiner*—Edward J Glick
*Assistant Examiner*—Thomas R Artman
(74) *Attorney, Agent, or Firm*—Armstrong Teasdale LLP

(57) ABSTRACT

A collimator control method for an X-ray CT apparatus includes changing an aperture of the collimator according to a position of a helical scan on the body axis of the subject in the progress of the helical scan.

12 Claims, 21 Drawing Sheets

Dr (0°, x, y)

D2 (0°, x, y)

FIG. 27
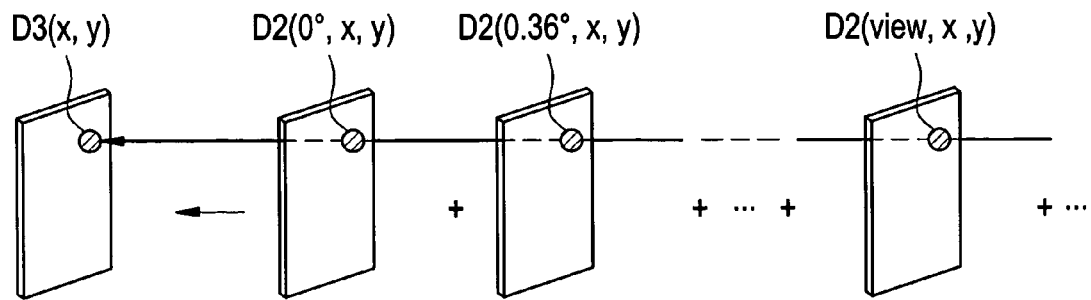
FIG. 28A
FIG. 28B
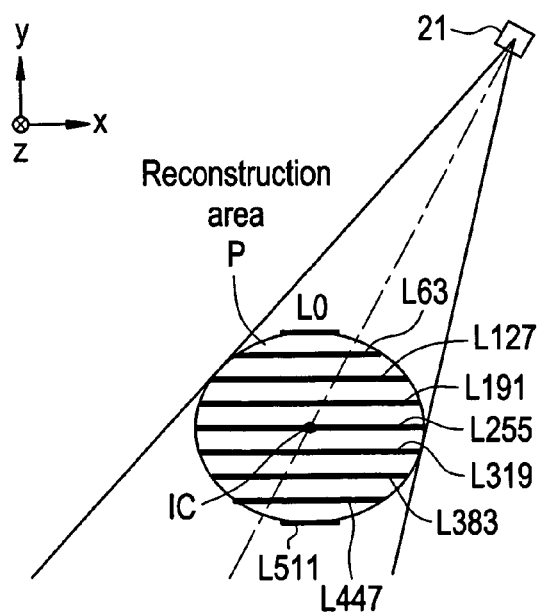
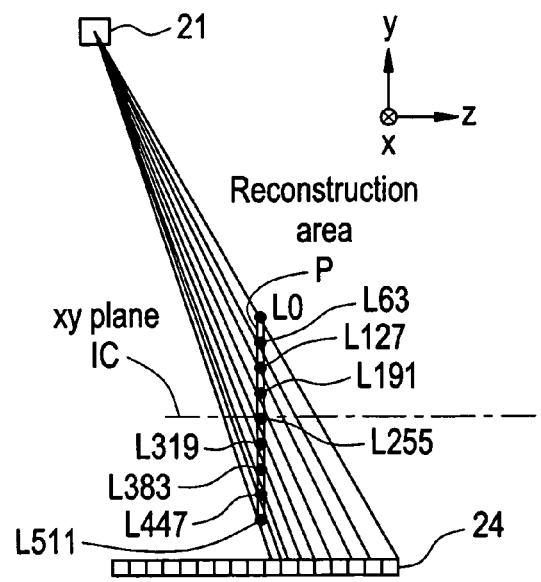

COLLIMATOR CONTROL METHOD AND X-RAY CT APPARATUS

CROSS REFERENCE TO RELATED APPLICATIONS

This application claims the benefit of Japanese Application No. 2004-2358899 filed Aug. 13, 2004.

BACKGROUND OF THE INVENTION

The present invention relates to a collimator control method and an X-ray CT (Computed Tomography) apparatus, and more specifically to a collimator control method for an X-ray CT apparatus, which helically scans a subject with an X-ray beam formed by a collimator, and an X-ray CT apparatus which performs collimator control.

When a helical scan is performed, an X-ray tube and an X-ray detector are rotated around a subject to be photographed and a table with the subject placed thereon is linearly moved. A multi-row detector or a plane X-ray detector is used as the X-ray detector and an X-ray beam is formed as a cone beam in association with it, so that the efficiency of acquisition of X-ray data through the helical scan is improved. A collimator for forming the X-ray beam as the cone beam has an aperture width held constant during the helical scan (refer to, for example, the following patent document 1).

[Patent Document 1] Japanese Unexamined Patent Publication No. 2003-052684 (Fifth page and FIG. 5)

Since X-ray data unused in image reconstruction are also acquired or collected at start and end points of the helical scan in the above X-ray CT apparatus, the irradiation of X rays corresponding thereto results in needless irradiation. Thus, the X-ray irradiation is not preferable in view of exposure of a patient.

SUMMARY OF THE INVENTION

Therefore, an object of the present invention is to realize a collimator control method which reduces exposure of a patient at the time of a helical scan and realizes an improvement in efficiency of X-ray data acquisition, and an X-ray CT apparatus which performs such collimator control.

(1) The invention according to one aspect for resolving the above problem provides a collimator control method for an X-ray CT apparatus wherein a subject is helically scanned in the direction of a body axis thereof using an X-ray beam formed by a collimator and image reconstruction is performed based on projection data obtained through an X-ray detector, comprising changing an opening degree of an aperture of the collimator according to a position on the body axis of the subject in the process of the progress of the helical scan.

(2) The invention according to another aspect for resolving the above problem provides an X-ray CT apparatus comprising an X-ray source, a collimator for shaping X-rays emitted from the X-ray source, control means for controlling the collimator, an X-ray detector disposed so as to be opposed to the X-ray source and the collimator with a subject interposed therebetween, and image reconstructing means for helically scanning the subject in the direction of a body axis thereof and reconstructing an image on the basis of projection data obtained through the X-ray detector, wherein the control means changes an opening degree of an aperture of the collimator according to a position of a helical scan on the body axis in the process of the progress of the helical scan.

It is preferable to, at a start position of the helical scan, open an aperture of the collimator at a first half of a predetermined collimator aperture width determined from a slice thickness in the direction of the progress of the helical scan and brings the aperture of the collimator into a closed state at its latter half, bring the aperture of the collimator into an opened state at both the first and latter halves in the progress direction of the helical scan halfway through the helical scan, and at an end position of the helical scan, close the aperture of the collimator at the first half in the progress direction of the helical scan and brings the aperture of the collimator into an opened state at its latter half, in that exposure of a patient is reduced to the minimum.

It is preferable to allow a change of the aperture of the collimator from the closed state to the opened state at the latter half thereof to be performed continuously and allow a change of the aperture from the opened state to the closed state to be performed continuously, in that they are adapted to a continuous change in data acquisition position.

It is preferable to allow a change of the aperture of the collimator from the closed state to the opened state to be performed at the latter half thereof during acceleration of the progress of the helical scan in the body-axis direction, and allow a change of the aperture of the collimator from the opened state to the closed state to be performed at the first half thereof during deceleration of the progress of the helical scan in the body-axis direction, in that exposure of the patient can be reduced similarly even though the collimator aperture is controlled during a constant velocity period.

The acceleration and deceleration of the progress of the helical scan in the body-axis direction may preferably be linear in that collimator control is easy. The acceleration and deceleration of the progress of the helical scan in the body-axis direction may preferably be nonlinear in that the acceleration and deceleration are smooth.

The X-ray detector may preferably be a multi-row X-ray detector or a plane X-ray detector in that the efficiency of the helical scan is improved. The X-ray CT apparatus may preferably perform image reconstruction by a three-dimensional image reconstructing method in that the quality of an image is improved.

In the invention according to each of the respective aspects, the opening degree of an aperture of a collimator is changed according to a position of a helical scan on a body axis in a progress process of the helical scan. It is therefore possible to realize a collimator control method which reduces exposure of a patient at the time of the helical scan and realizes an improvement in efficiency of X-ray data acquisition, and an X-ray CT apparatus which performs such collimator control.

Further objects and advantages of the present invention will be apparent from the following description of the preferred embodiments of the invention as illustrated in the accompanying drawings.

BRIEF DESCRIPTION OF THE DRAWINGS

FIG. 27 is an explanatory diagram illustrating a state in which backprojection data D2 are added corresponding to pixels over all views to obtain backprojection data D3.

FIGS. 28a and 28b are conceptual diagrams showing a state in which lines on a circular reconstruction area are projected in an X-ray penetration direction.

DETAILED DESCRIPTION OF THE INVENTION

Figure 1:
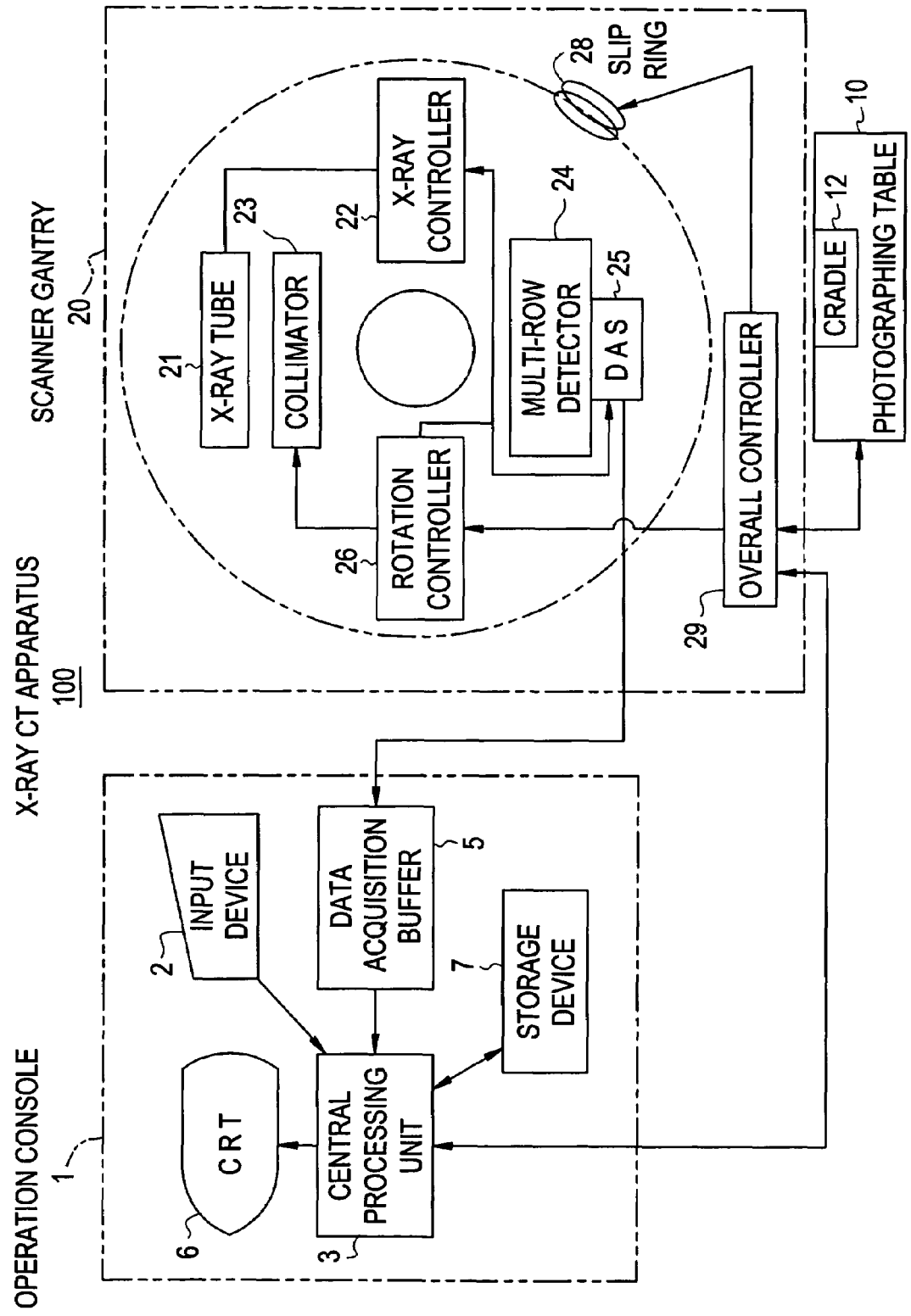
FIG. 1 is a block diagram showing an X-ray CT apparatus illustrative of one example of the best mode for carrying out the present invention.

Best modes for carrying out the invention will be explained below with reference to the accompanying drawings. Incidentally, the present invention is not limited to the best modes for carrying out the invention. A block diagram of an X-ray CT apparatus is shown in FIG. 1. The present apparatus is one example showing the best mode for carrying out the present invention. One example of the best mode for carrying out the present invention related to the X-ray CT apparatus is shown by the configuration of the present apparatus. One example of the best mode for carrying out the present invention related to a collimator control method is shown by the operation of the present apparatus.

The X-ray CT apparatus 100 is equipped with an operation console 1, a photographing table 10 and a scan gantry 20. The operation console 1 is equipped with an input device 2 which accepts an input from an operator, a central processing unit 3 which executes an image reconstructing process or the like, a data acquisition buffer 5 which acquires or collects projection data acquired by the scan gantry 20, a CRT 6 which displays a CT image reconstructed from the projection data, and a storage device 7 which stores programs, data and X-ray CT images therein. The central processing unit 3 is one example of an image reconstructing means according to the present invention.

The table device 10 is provided with a cradle 12 which inserts and draws a subject into and from a bore (cavity portion) of the scan gantry 20 with the subject placed thereon. The cradle 12 is elevated and moved linearly along the table by a motor built in the photographing table 10. Coordinates in a Z-axis direction are counted by an encoder. The corresponding z-axis coordinate is calculated by a controller 29. The controller 29 adds a z-axis coordinate Z (view, i) corresponding to a center coordinate in a z direction of a detector to its corresponding projection data (view, j, i) of a DAS through a slip ring 28. Here, a channel number, a detector row or sequence and a view angle are assumed to be i, j and view respectively.

The scan gantry 20 is equipped with an X-ray tube 21, an X-ray controller 22, a collimator 23, a multi-row detector 24, the DAS (Data Acquisition System) 25, a rotation controller 26 which rotates the X-ray tube 21 or the like about a body axis of the subject and controls the collimator 23, and the controller 29 which performs the transfer of control signals or the like between the operation console 1 and the photographing table 10.

The X-ray tube 21 is one example of an X-ray source according to the present invention. The collimator 23 is one example of a collimator according to the present invention. The rotation controller 26 is one example of a control means according to the present invention. The multi-row detector 24 is one example of an X-ray detector according to the present invention.

Figure 2:
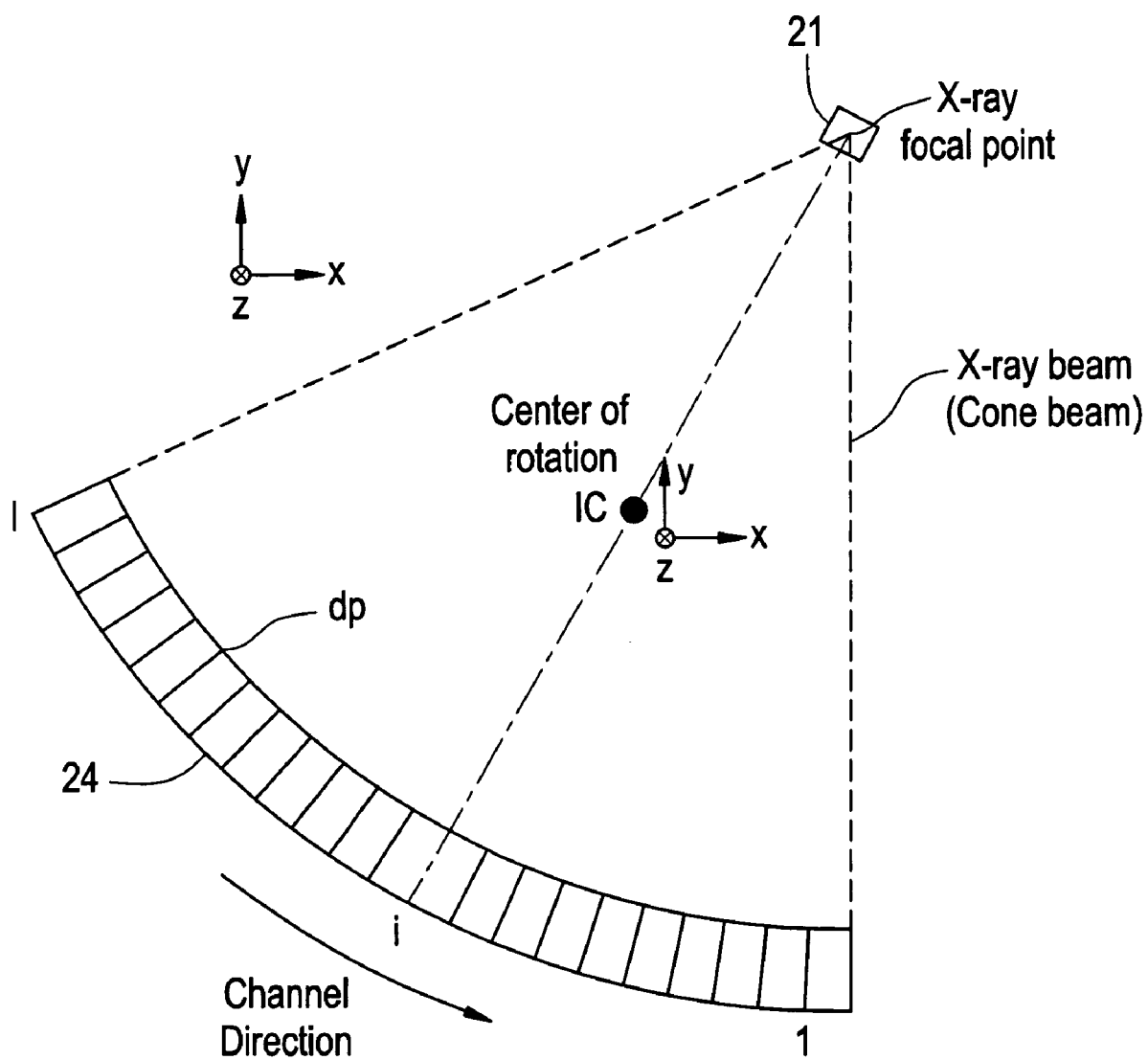
FIG. 2 is an explanatory diagram illustrating rotation of an X-ray tube and a multi-row detector.

FIG. 2 is an explanatory view showing the X-ray tube 21 and the multi-row detector 24. The X-ray tube 21 and the multi-row detector 24 rotate about the center of rotation IC. When the vertical direction is assumed to be a y direction, the horizontal direction is assumed to be an x direction and the direction orthogonal to these is assumed to be a z direction, the plane of rotation of each of the X-ray tube 21 and the multi-row detector 24 is an xy plane. The direction of movement of the cradle 12 corresponds to the z direction.

An X-ray beam called cone beam CB is generated by the X-ray tube 21 and the collimator 23. When the direction of a center axis of the cone beam CB is parallel to a y direction, the view angle is assumed to be equal to 0°. The multi-row detector 24 has detector rows corresponding to 256 rows, for example. The direction of side-by-side provision of the detector rows corresponds to the z direction. The respective detector rows respectively have channels corresponding to 1024 channels, for example.

Figure 3:
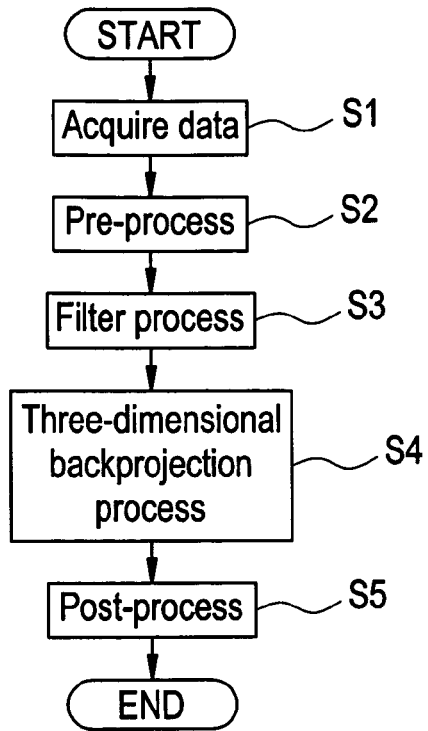
FIG. 3 is a flow diagram showing a schematic operation of the X-ray CT apparatus.

FIG. 3 is a flow diagram schematically showing the operation of the X-ray CT apparatus 100. In Step S1, a table linear movement position z and projection data D (view, j, i) expressed in the view angle view, detector row number j and channel number i are acquired while the X-ray tube 21 and the multi-row detector 24 are being rotated about a subject to be photographed and the cradle 12 is being linearly moved along the table.

That is, the acquisition of data by a helical scan is performed. Incidentally, the coordinate of the photographing table in the z-axis direction at this time results in one obtained by adding z-coordinate information Z (view) of the photographing table at the center position in the z direction, of the data acquisition system comprised of the multi-row detector 24 and the X-ray tube 21 to the corresponding projection data D0 (view, j, i). A data acquisition process in Step S1 will be explained with reference to FIGS. 5 through 21.

Figure 4:
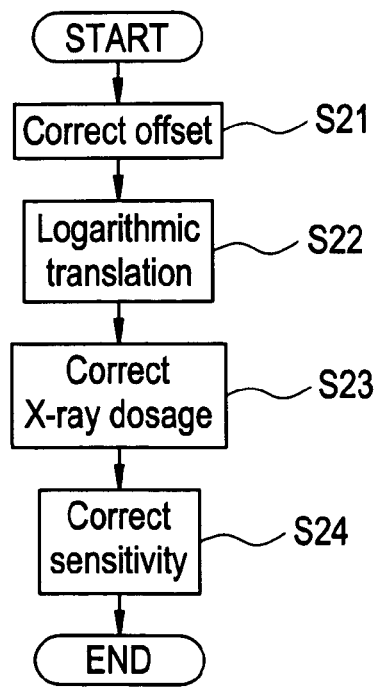
FIG. 4 is a flow diagram depicting part of the schematic operation of the X-ray CT apparatus.

In Step S2, the projection data D0 (view, j, i) is pre-processed. The details of the pre-processing include an offset correction (Step S21), logarithmic translation (Step S22), an X-ray dosage correction (Step S23) and a sensitivity correction (Step S24) as shown in FIG. 4.

In Step S3, a reconstruction function superimposition process is effected on the pre-processed projection data D2 (view, j, i). That is, the projection data is Fourier-transformed and multiplied by a reconstruction function, followed by being inversely Fourier-transformed.

In Step S4, a three-dimensional backprojection process is performed on the projection data D0 (view, j, i) subjected to the reconstruction function superimposition process to determine backprojection data D3 (x, y). The three-dimensional backprojection process will be described later with reference to FIG. 22.

In Step S5, the backprojection data D3 (x, y) is post-processed to obtain a CT image.

Figure 5:
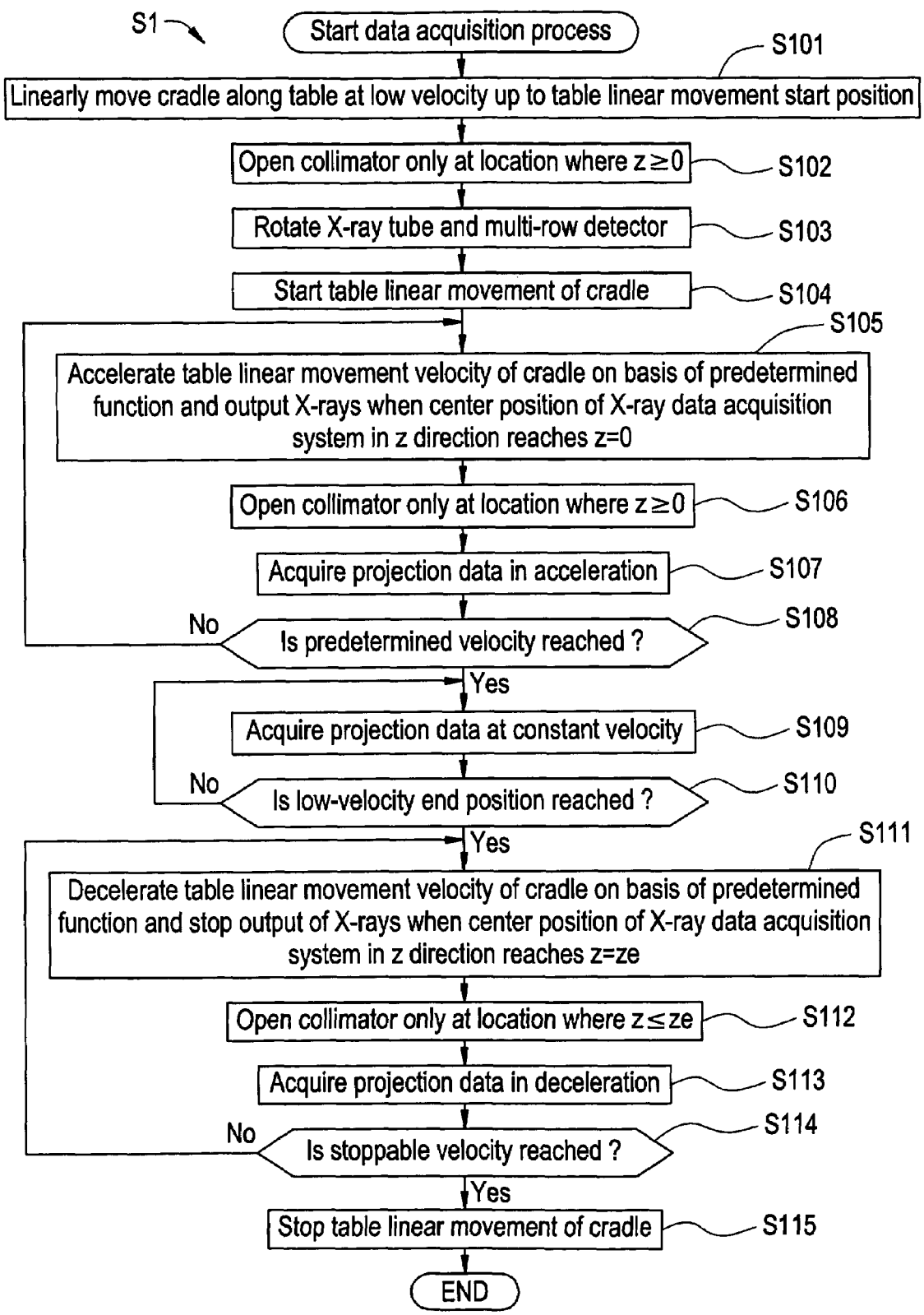
FIG. 5 is flow diagram showing the details of a data acquisition process.
Figure 6:
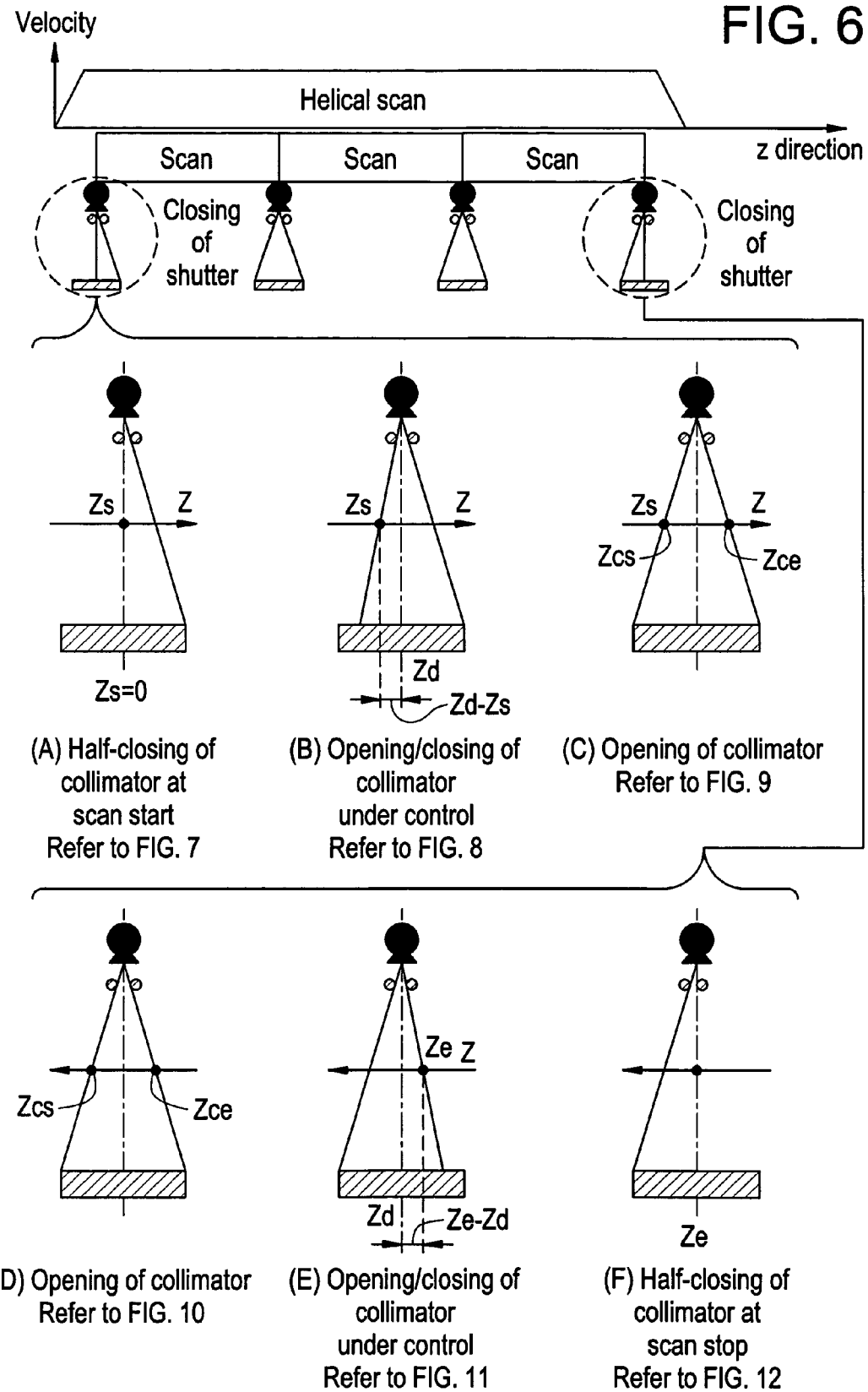
FIGS. 6a, 6b, 6c, 6d, 6e, and 6f are explanatory diagrams depicting an operation of a collimator.

FIG. 5 is a flow diagram showing the details of the data acquisition process (Step S1 in FIG. 3). Controlled states of an aperture of the collimator 23 at data acquisition are shown in FIG. 6 and FIGS. 7 through 12.

Figure 14:
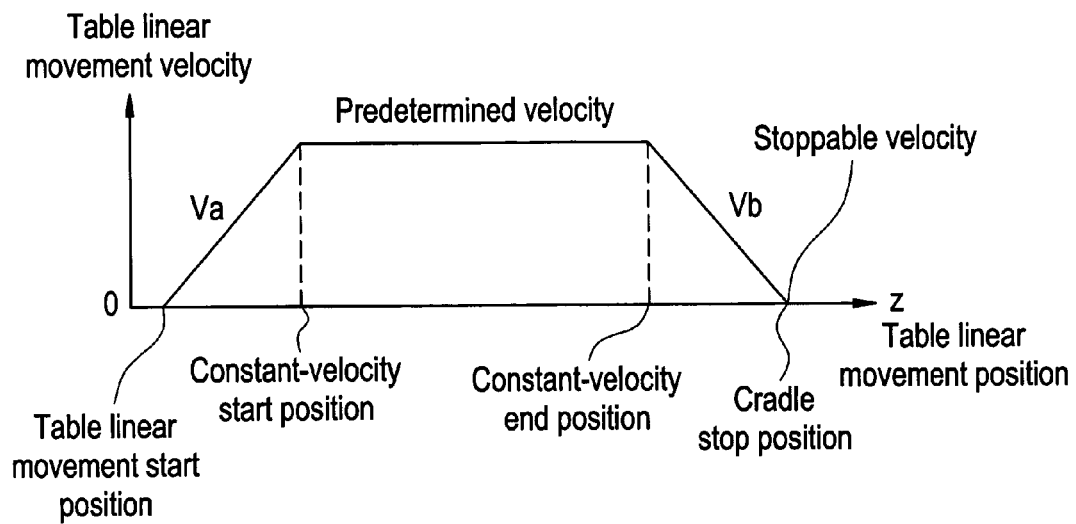
FIG. 14 is a graph illustrating a change in table linear movement velocity where acceleration and deceleration are linearly performed.
Figure 16:
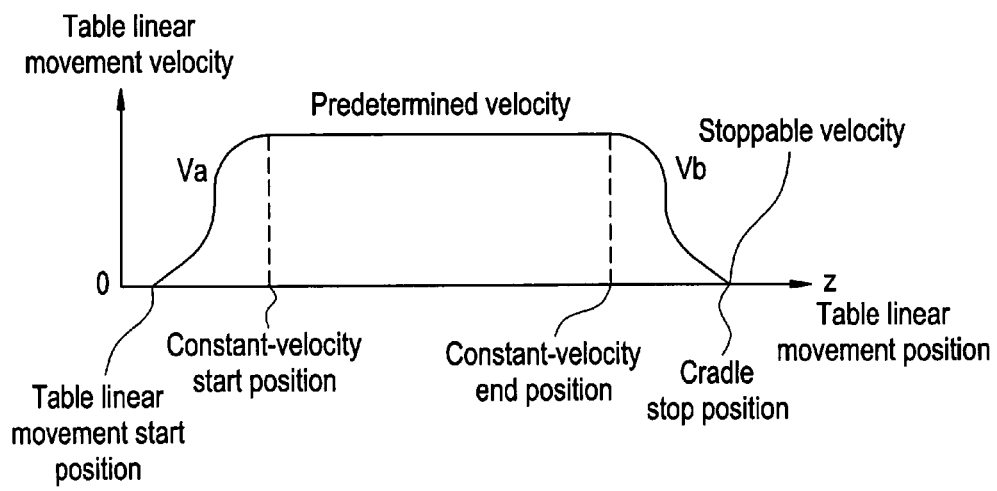
FIG. 16 is a graph showing a change in table linear movement velocity where acceleration and deceleration are nonlinearly performed.

In Step S101, the cradle 12 linearly moves along the table up to table linear movement start positions shown in FIGS. 14 and 16 at low velocity.

Figure 7:
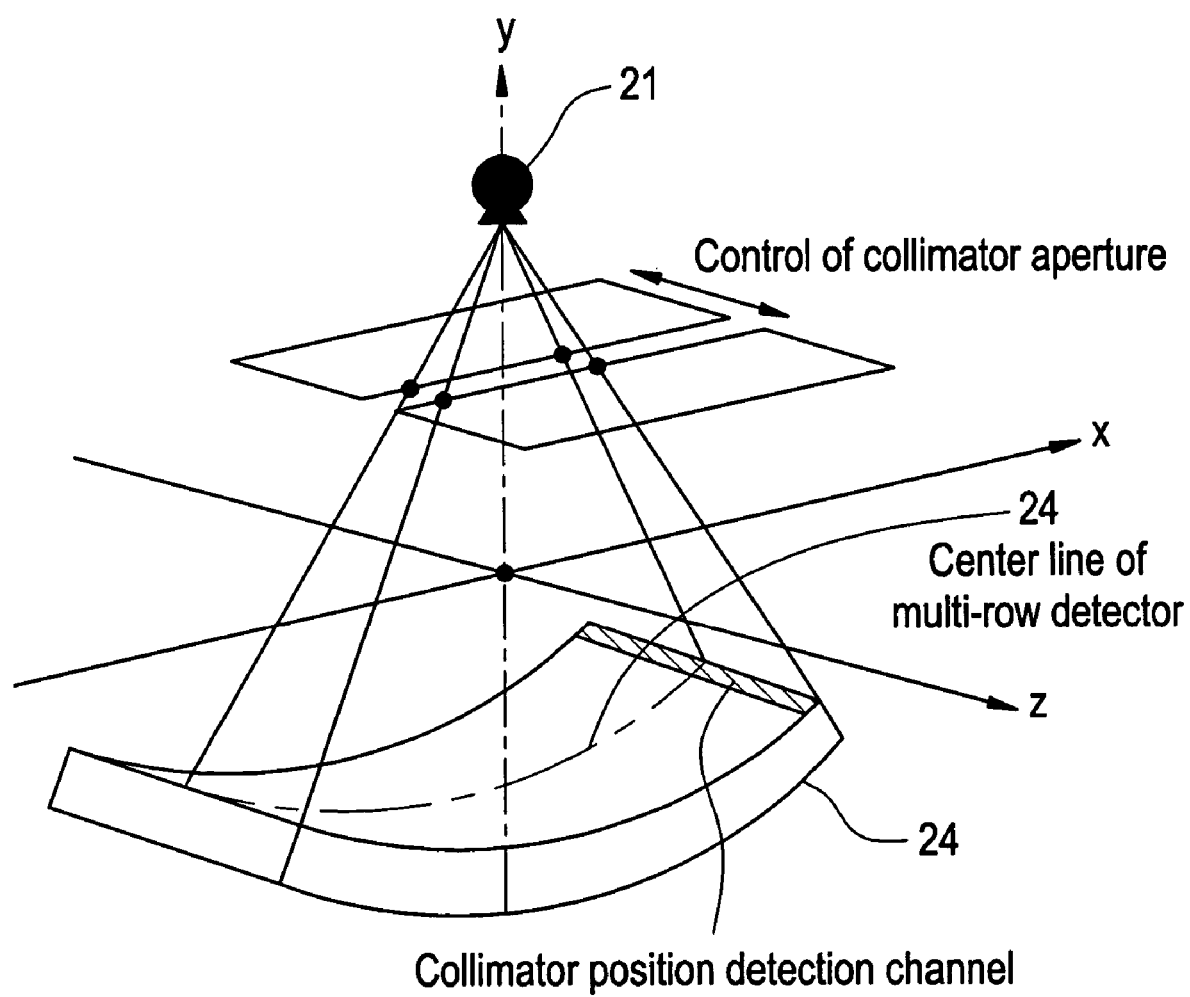
FIG. 7 is an explanatory diagram showing another operation of the collimator.

In Step S102, the collimator is kept open only at a location where z≧0 at the position of the center of rotation IC. This condition is shown in FIG. 6(A) and FIG. 7. Incidentally, the sign of z relates to the center of rotation IC, the direction in which the helical scan proceeds is assumed to be + (front side) and its opposite direction is assumed to be − (rear side).

In Step S103, the X-ray tube 21 and the multi-row detector 24 are rotated about the subject to be photographed with IC as the center of rotation.

In Step S104, the table linear movement of the cradle 12 is started.

Figure 15:
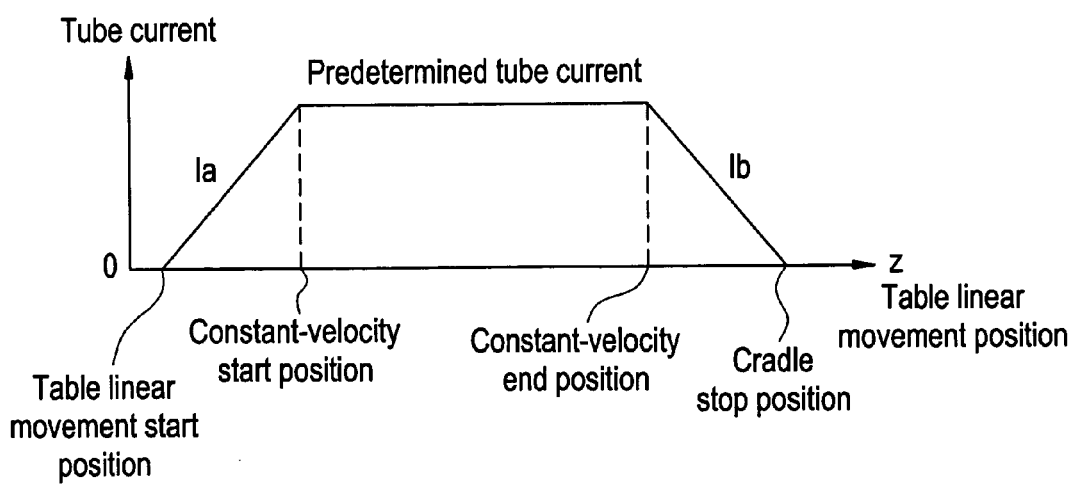
FIG. 15 is a graph depicting a change in tube current where acceleration and deceleration are linearly performed.
Figure 17:
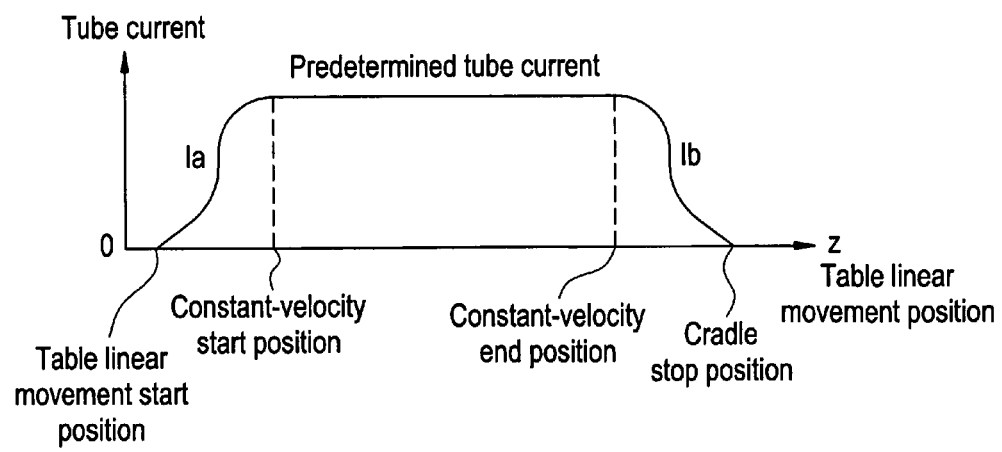
FIG. 17 is a graph illustrating a change in tube current where acceleration and deceleration are nonlinearly performed.
Figure 18:
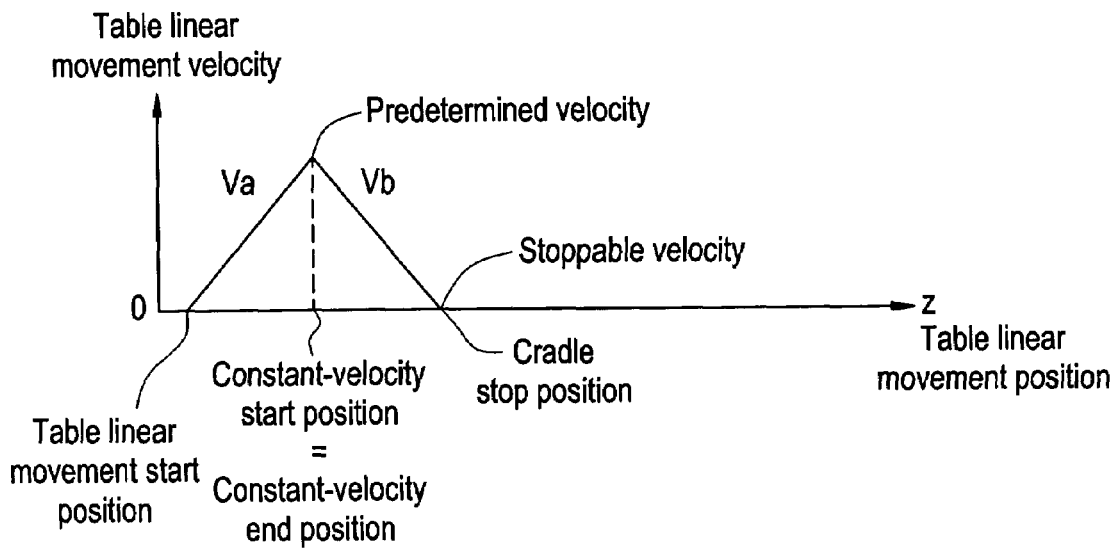
FIG. 18 is a graph showing a change in table linear movement velocity where acceleration and deceleration are linearly performed without a constant velocity interval.
Figure 19:
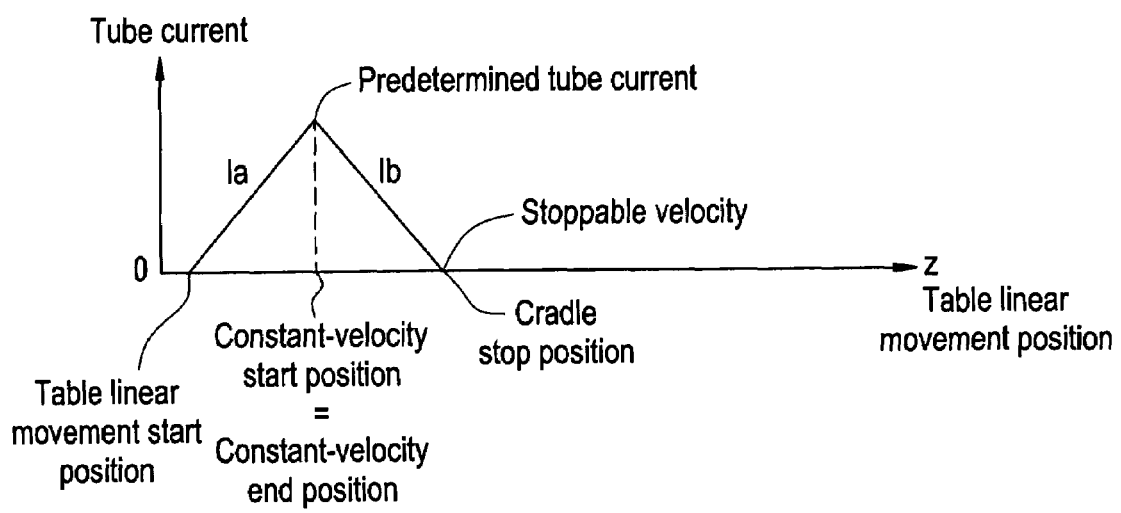
FIG. 19 is a graph illustrating a change in tube current where acceleration and deceleration are linearly performed without a constant velocity interval.
Figure 20:
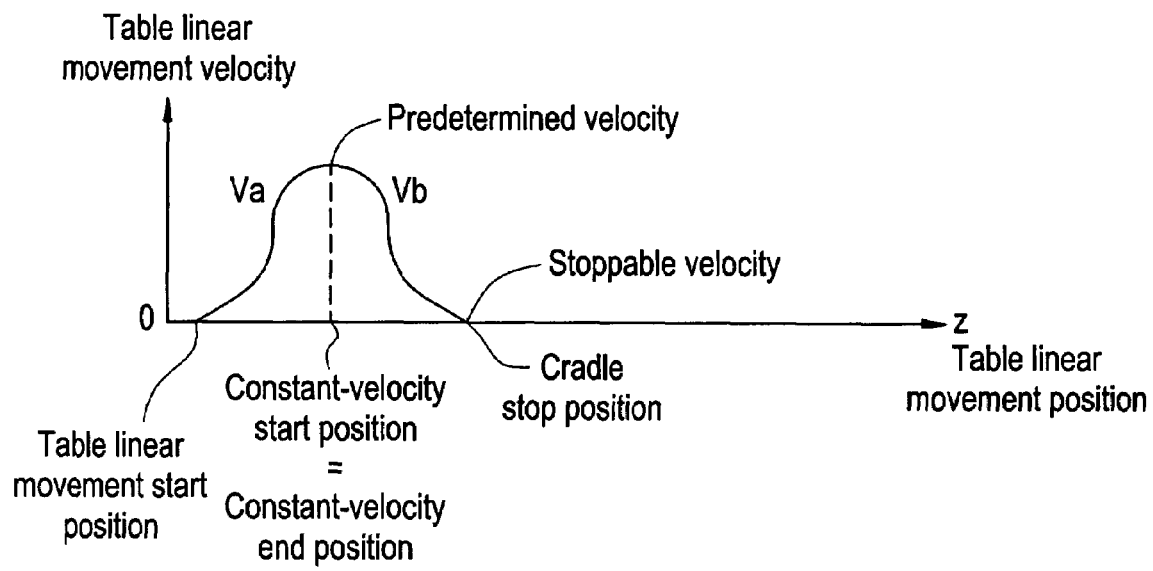
FIG. 20 is a graph depicting a change in table linear movement velocity where acceleration and deceleration are nonlinearly performed without a constant velocity interval.
Figure 21:
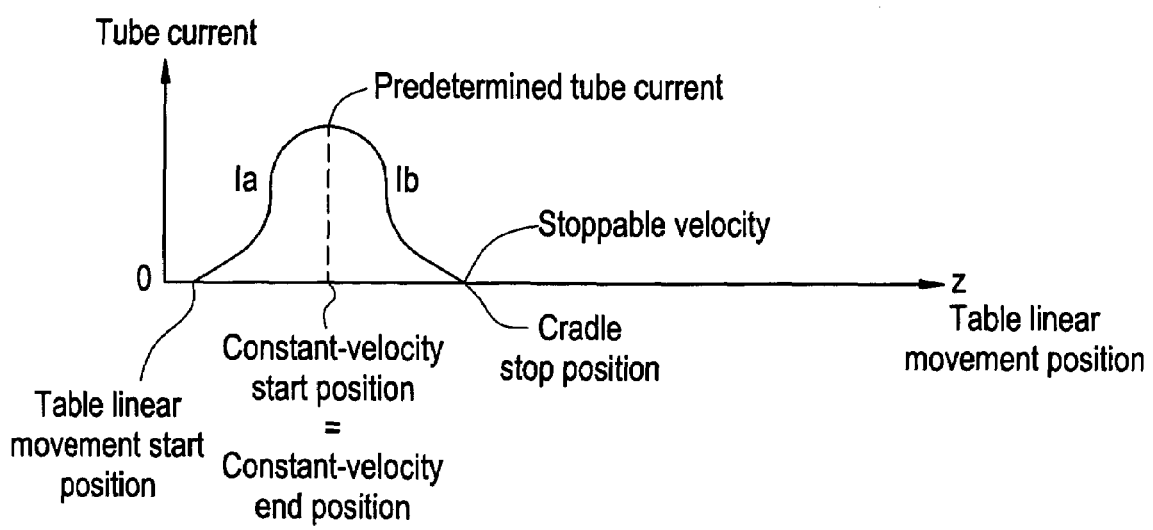
FIG. 21 is a graph showing a change in tube current where acceleration and deceleration are nonlinearly performed without a constant velocity interval.

In Step S105, the velocity of the table linear movement of the cradle 12 is accelerated on the basis of a predetermined function. A case in which the predetermined function is linear relative to the time, is shown in FIGS. 14 and 15, and a case in which the predetermined function is nonlinear relative to the time, is shown in FIGS. 16 and 17. When the position of center of the X-ray data acquisition system in the z direction reaches z=0, X rays are outputted.

With the output thereof, the following control of collimator's aperture is performed. Assuming that the opening/closing states of the collimator at this time are as follows:

cw: collimator aperture width (aperture),

Zce: z coordinate maximum value of collimator aperture (+ side), and

Zcs: z coordinate minimum value of collimator aperture (− side), cw=Zce−Zcs is reached.

Also assuming that Zd, Zs and Ze are set as follows:

Zd: center z coordinate of data acquisition system,

Zs: z coordinate at the start of helical scan (Zs=0), and

Ze: z coordinate at the stop of helical scan,

Zce is set to a z coordinate equivalent to the first half of a pre-set slice thickness at an X-ray data acquisition start position and controlled so that Zcs=Zs is reached. This condition is illustrated in FIG. 6(A) and FIG. 7. Thus, the first half of the aperture is opened and the latter half thereof is brought into a closed state.

Figure 12:
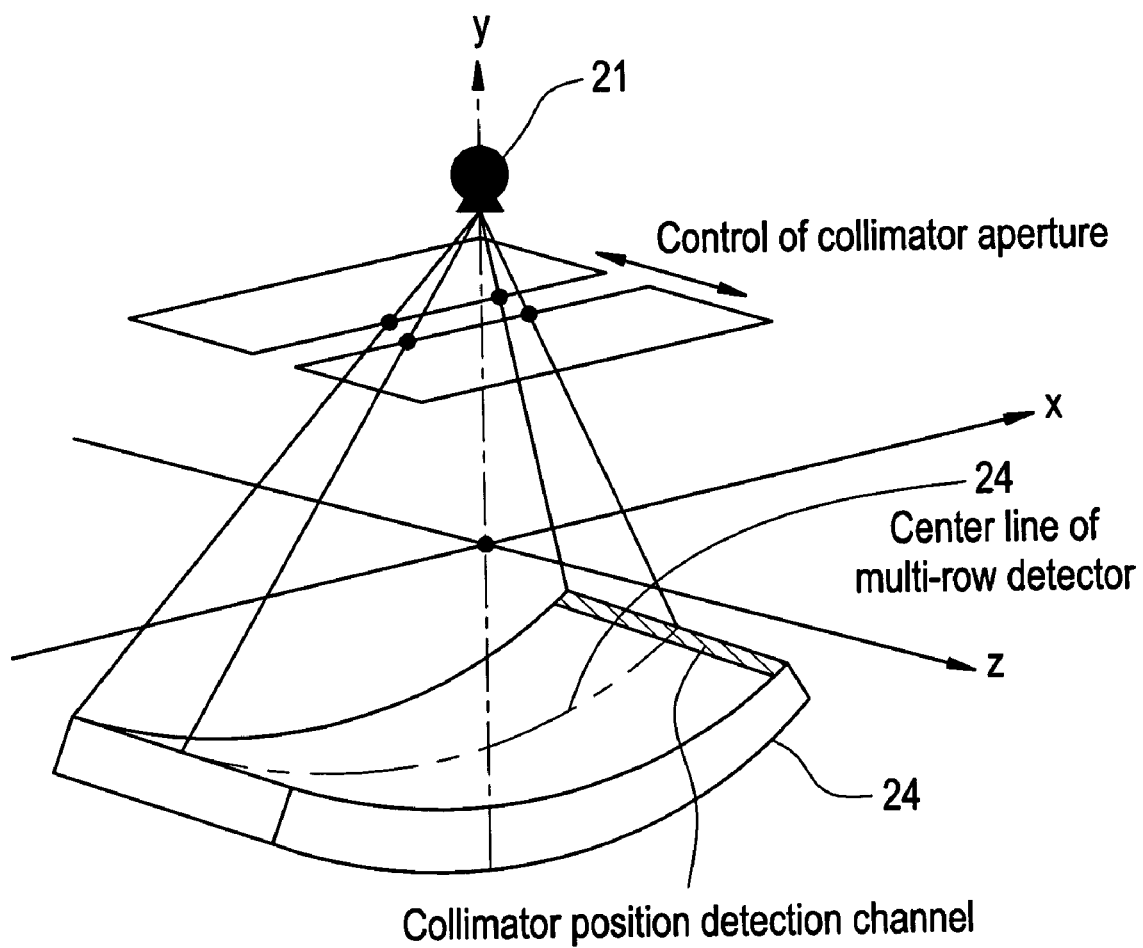
FIG. 12 is an explanatory diagram depicting a still further operation of the collimator.
Figure 13:
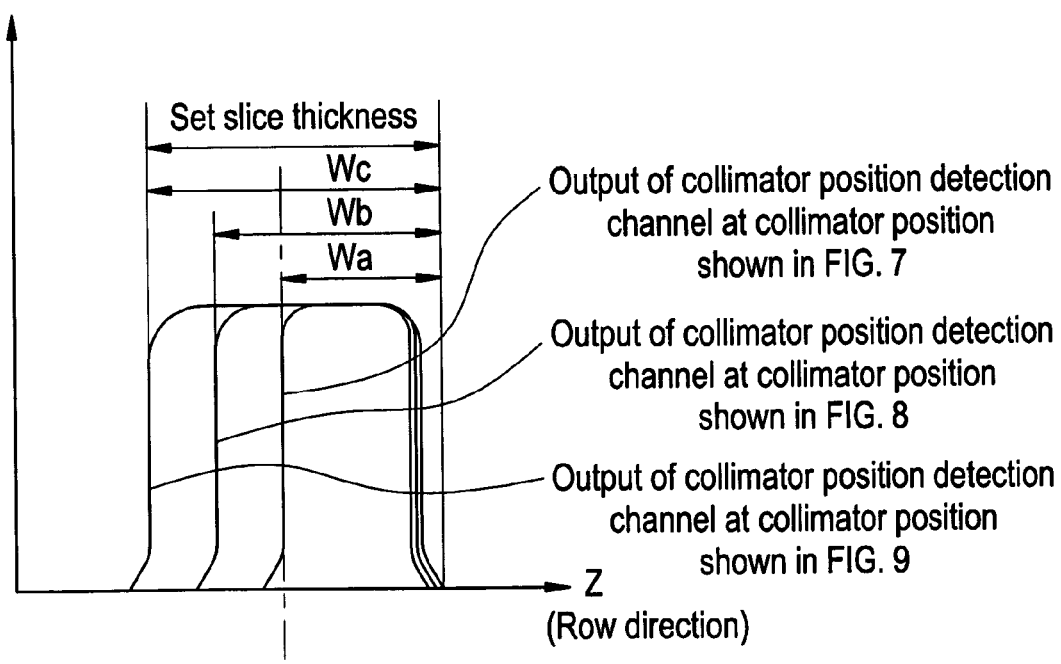
FIG. 13 is an explanatory diagram showing outputs of collimator position detection channels at respective collimator positions.

The state of opening/closing of the collimator is measured using each of collimator position detection channels (portions indicated by broken lines) shown in FIGS. 7 through 12. When the outputs of the corresponding channel are taken along the z direction (row direction), they are represented as shown in FIG. 13. The states of opening and closing of the collimator can be recognized by determining widths wa, wb and wc with which detector output signals at this time are outputted.

At this time, each of the z-direction coordinates counted by the encoder for determining the z-direction coordinates of the photographing table 10 is calculated as a z-axis coordinate by the controller 29, which in turn reach the DAS 25 through the slip ring 28.

The DAS 25 is capable of recognizing the present opening/closing state of the collimator from each of the outputs of the collimator position detection channels. The rotation controller 26 issues a command to the collimator 23 in such a manner that the collimator is opened or closed to a collimator opening/closing target value determined from each of the z coordinates.

The difference between a collimator opening/closing value determined from each of the outputs of the collimator position detection channels and the collimator opening/closing target value is determined to generate a feedback signal. The rotation controller 29 issues instructions to the collimator 23 in accordance with the feedback signal to thereby perform feedback control which determines whether the collimator 23 has acted on instructions.

In Step S106, the collimator is kept open only at a location where when z≧0. That is, the collimator is controlled in such a manner that Zcs=Zs=0 is reached. This condition is represented as shown in FIG. 6(A) and FIG. 7.

Figure 8:
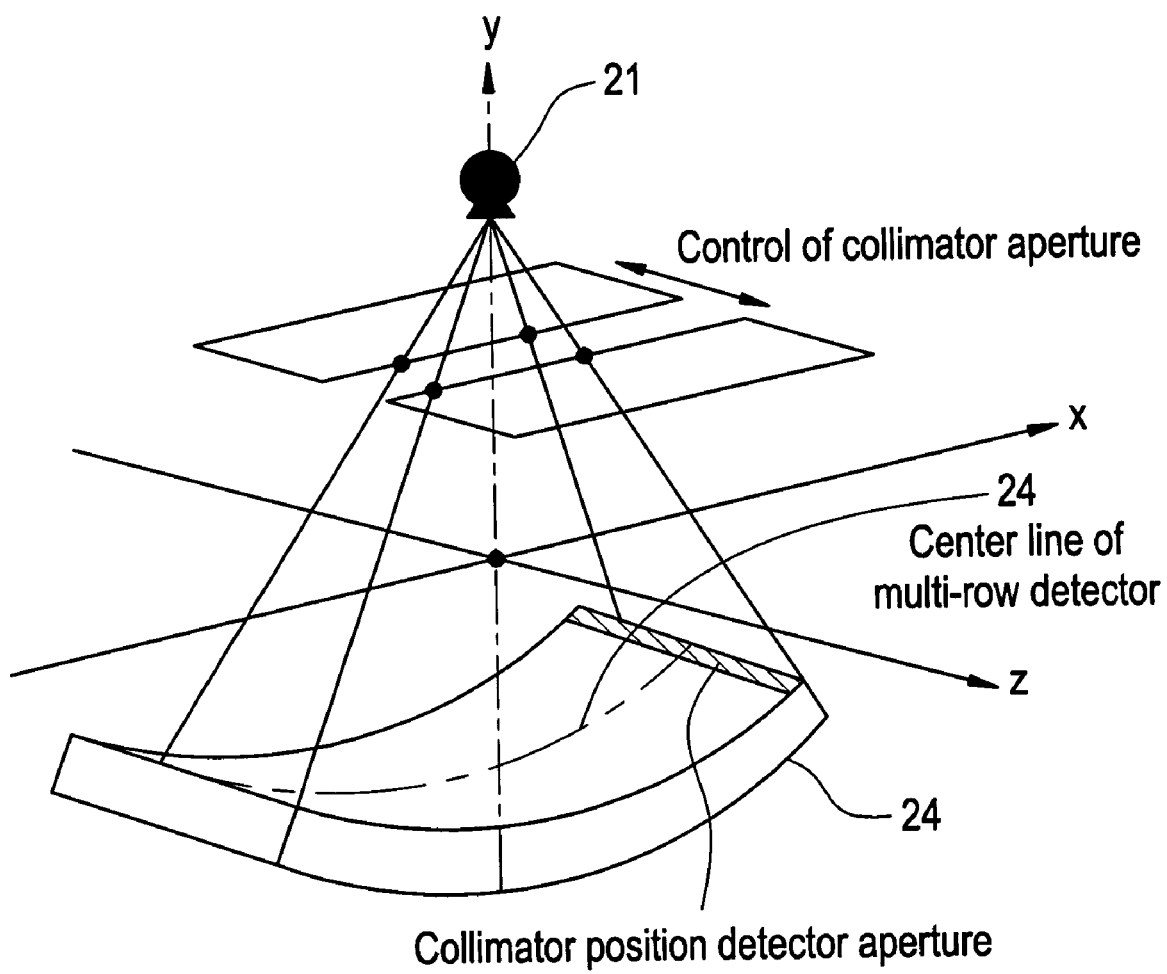
FIG. 8 is an explanatory diagram illustrating a further operation of the collimator.

In Step S107, projection data D0 (view, j, i) in acceleration is acquired. At this time, the latter half of the aperture is opened with the progress of the helical scan. The latter half thereof is opened with an increase in the difference between Zs and Zd as shown in FIG. 6(B). This state is illustrated in FIG. 8.

In Step S108, it is determined whether the table linear movement velocity of the cradle 12 reaches a predetermined velocity Vc shown in FIGS. 14 and 16. When the table linear movement velocity reaches the predetermined velocity Vc, the X-ray CT apparatus 100 proceeds to Step S109. When the table linear movement velocity is found not to reach the predetermined velocity Vc, the X-ray CT apparatus 100 is returned to Step S104, where the table linear movement velocity is further accelerated.

Figure 9:
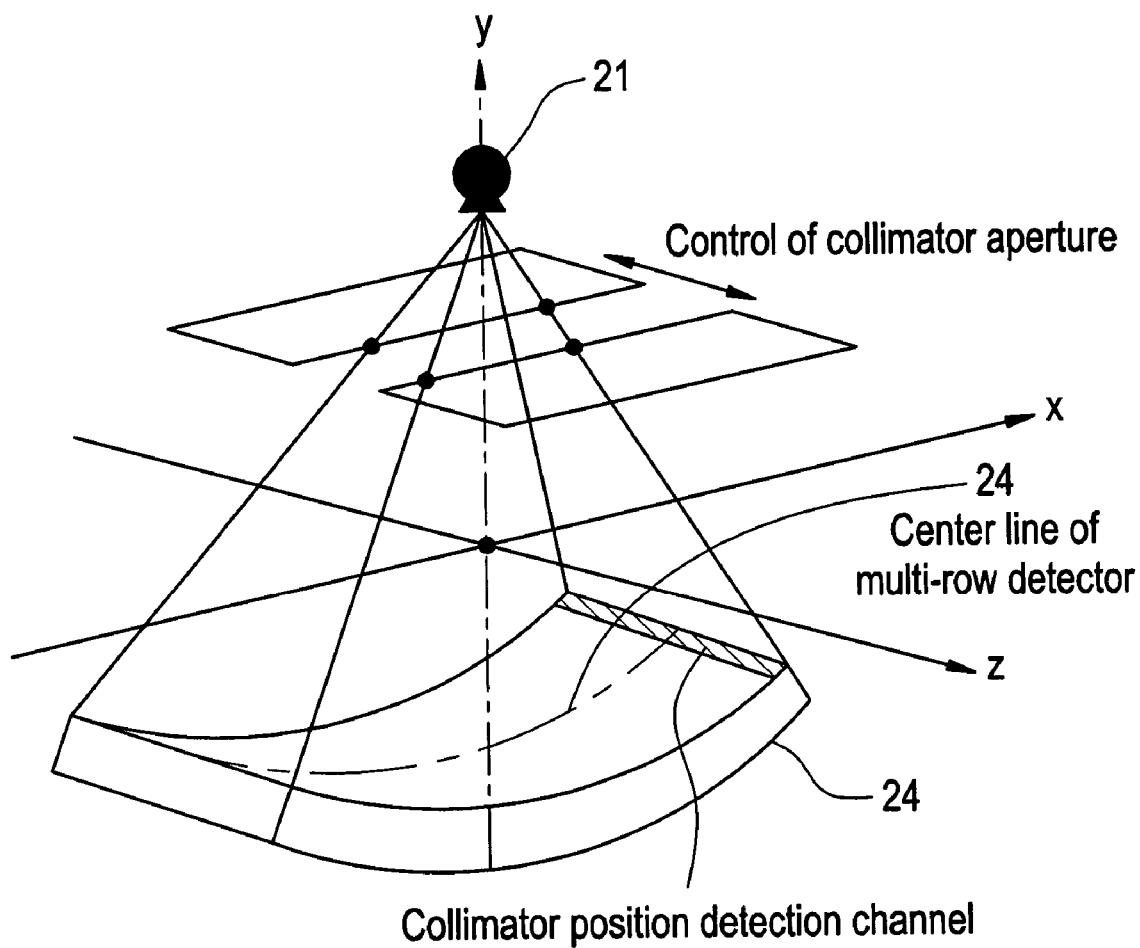
FIG. 9 is an explanatory diagram depicting a still further operation of the collimator.
Figure 10:
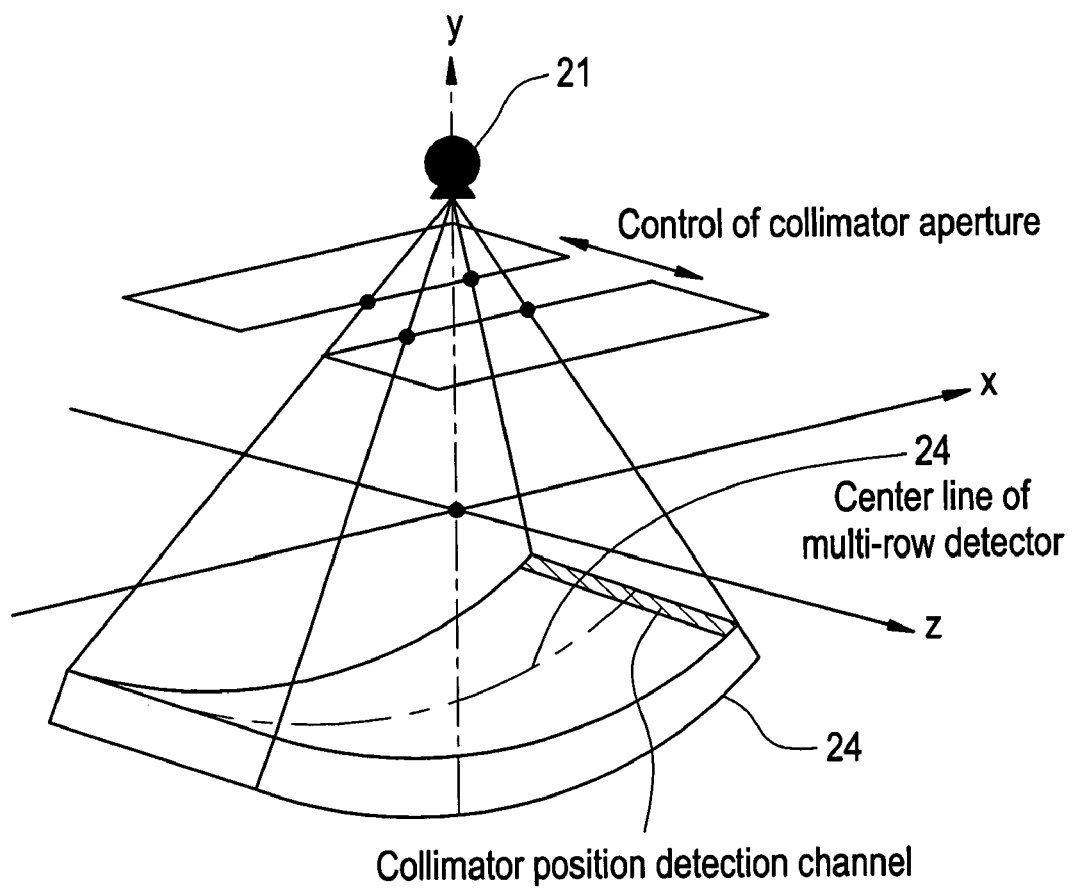
FIG. 10 is an explanatory diagram showing a still further operation of the collimator.
Figure 11:
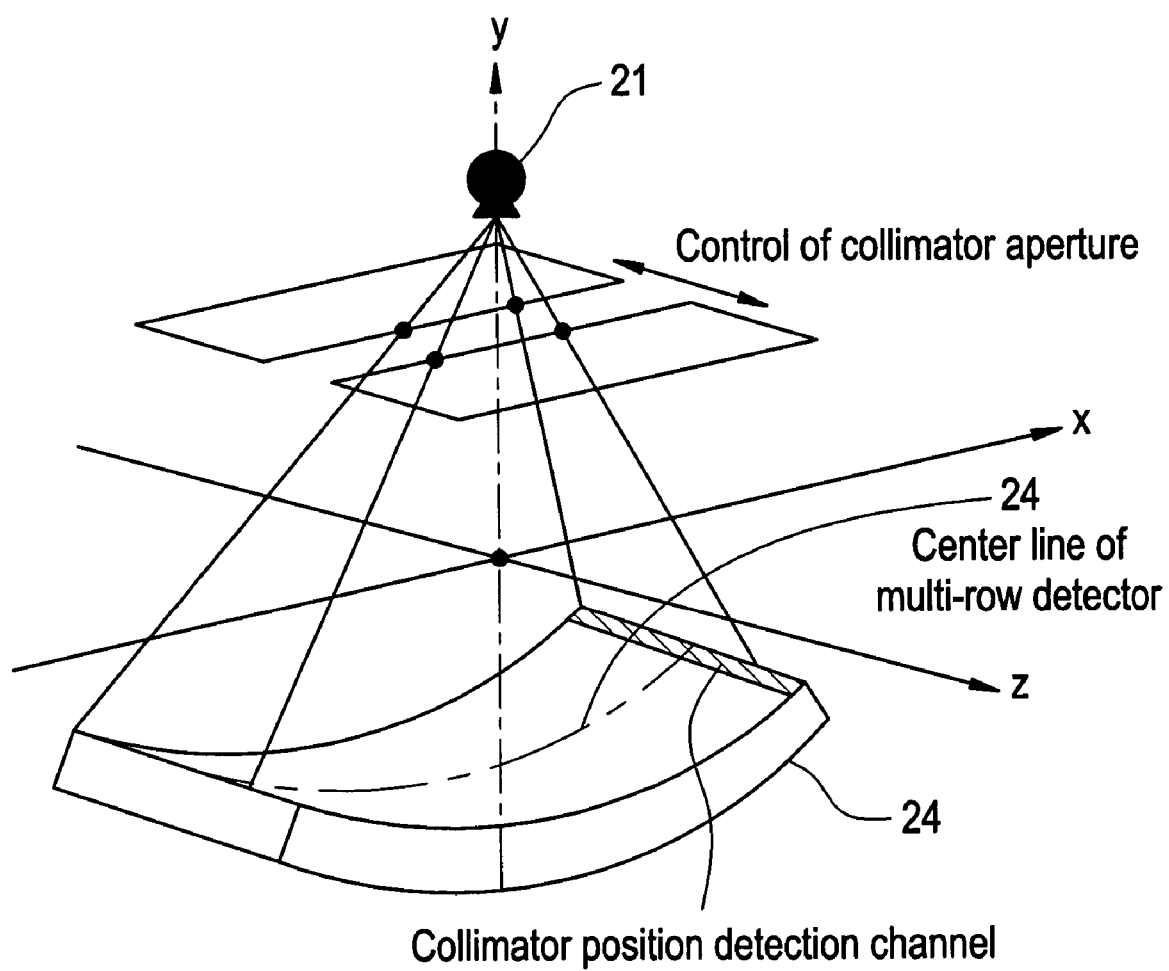
FIG. 11 is an explanatory diagram illustrating a still further operation of the collimator.

In Step S109, projection data D0 (view, j, i) at low velocity is acquired in a state in which the table linear movement velocity of the cradle 12 is being maintained at a predetermined velocity. At this time, the latter half of the aperture is completely opened up. Thus, the first and latter halves of the aperture are both placed in an opened-up state. This condition is illustrated in FIG. 6(C) and FIG. 9.

In Step S110, it is determined whether the cradle 12 reaches a constant-velocity end position shown in each of FIGS. 14 and 16. When the cradle 12 has reached the constant-velocity end position, the X-ray CT apparatus 100 proceeds to Step 111. When it is determined that the cradle 12 does not reach the constant-velocity end position, the X-ray CT apparatus 100 is returned to Step S109, where the acquisition of projection data at constant velocity is continued.

In Step S111, the table linear movement velocity of the cradle 12 is decelerated based on a predetermined function and a tube current is reduced correspondingly. A case in which the predetermined function is linear, is shown in FIGS. 14 and 15. A case in which the predetermined function is non-linear, is shown in FIGS. 16 and 17.

When, at this time, the coordinate Zce on the maximum value side in the z direction, of the collimator of the X-ray data acquisition system begins to reach the coordinate Ze at the stop of the helical scan, the X-ray CT apparatus starts controlling the opening/closing of the collimator such that Zce=Ze is reached. That is, the X-ray CT apparatus starts to gradually close the first half of the aperture. This condition is illustrated in FIGS. 6(D) and 6(E) and FIGS. 10 and 11.

When the center coordinate of the X-ray data acquisition system reaches Zd=Ze, the output of X rays is stopped. This condition is illustrated in FIG. 6(F) and FIG. 12. Thus, the first half of the aperture is closed and the latter half thereof is brought into a closed state.

In Step S112, the collimator is kept open only at a location where $Z \leq Ze$. That is, the collimator is controlled in such a manner that Zce=Ze is reached. This condition is represented as shown in FIG. 6(F) and FIG. 12.

In Step S113, projection data D0 (view, j, i) placed under deceleration is acquired.

In Step S114, it is determined whether the table linear movement velocity of the cradle 12 reaches a stoppable velocity shown in each of FIGS. 14 and 16. When the stoppable velocity is reached, the X-ray CT apparatus proceeds to Step S115. When the stoppable velocity is not reached, the X-ray CT apparatus returns to Step S11, where the table linear movement velocity is decelerated.

In Step S115, the table linear movement of the cradle 12 is stopped.

Incidentally, if the constant velocity start position is set to be equal to the constant velocity end position as shown in FIGS. 18 through 21, then the projection data D0 (view, j, i) can be acquired at the shortest table linear movement distance. Even in the case of such a scan, collimator control, which conforms to the above, is performed.

Thus, since only the first half of the aperture is kept open and the latter half thereof is closed at the start of the helical scan, the dose of exposure of a patient can be reduced correspondingly. Since only the latter half of the aperture is made open and the first half thereof is closed at the end of the helical scan, the dose of exposure of the patient can be reduced correspondingly. It is thus possible to set the patient's exposure to a required minimum.

A change of the aperture at the latter half from the closed state thereof to the opened state thereof is continuously performed, and a change of the aperture at the first half thereof from the opened state thereof to the closed state thereof is continuously performed. This can therefore adapt to a continuous change in data acquisition position.

The change of the aperture at the latter half from the closed state thereof to the opened state thereof is made during acceleration of the progress of the helical scan in the body-axis direction, and the change of the aperture at the first half from the opened state thereof to the closed state thereof is made during deceleration of the progress of the helical scan in the body-axis direction. It is therefore possible to improve the efficiency of the helical scan.

Making linear the acceleration and deceleration of the progress of the helical scan in the body-axis direction enables the collimator to be easily controlled. Incidentally, the acceleration and deceleration can be smoothed by making nonlinear the acceleration and deceleration of the progress of the helical scan in the body-axis direction.

Since the X-ray detector is of a multi-row X-ray detector or a plane X-ray detector, the efficiency of the helical scan can be improved.

Even though such collimator control is done, the complete data set from the scan start position Zs to the scan end position Ze is acquired as the projection data. Accordingly, a complete reconstructed image can be obtained with respect to the range from the scan start position Zs to the scan end position Ze on the basis of these projection data.

Figure 22:
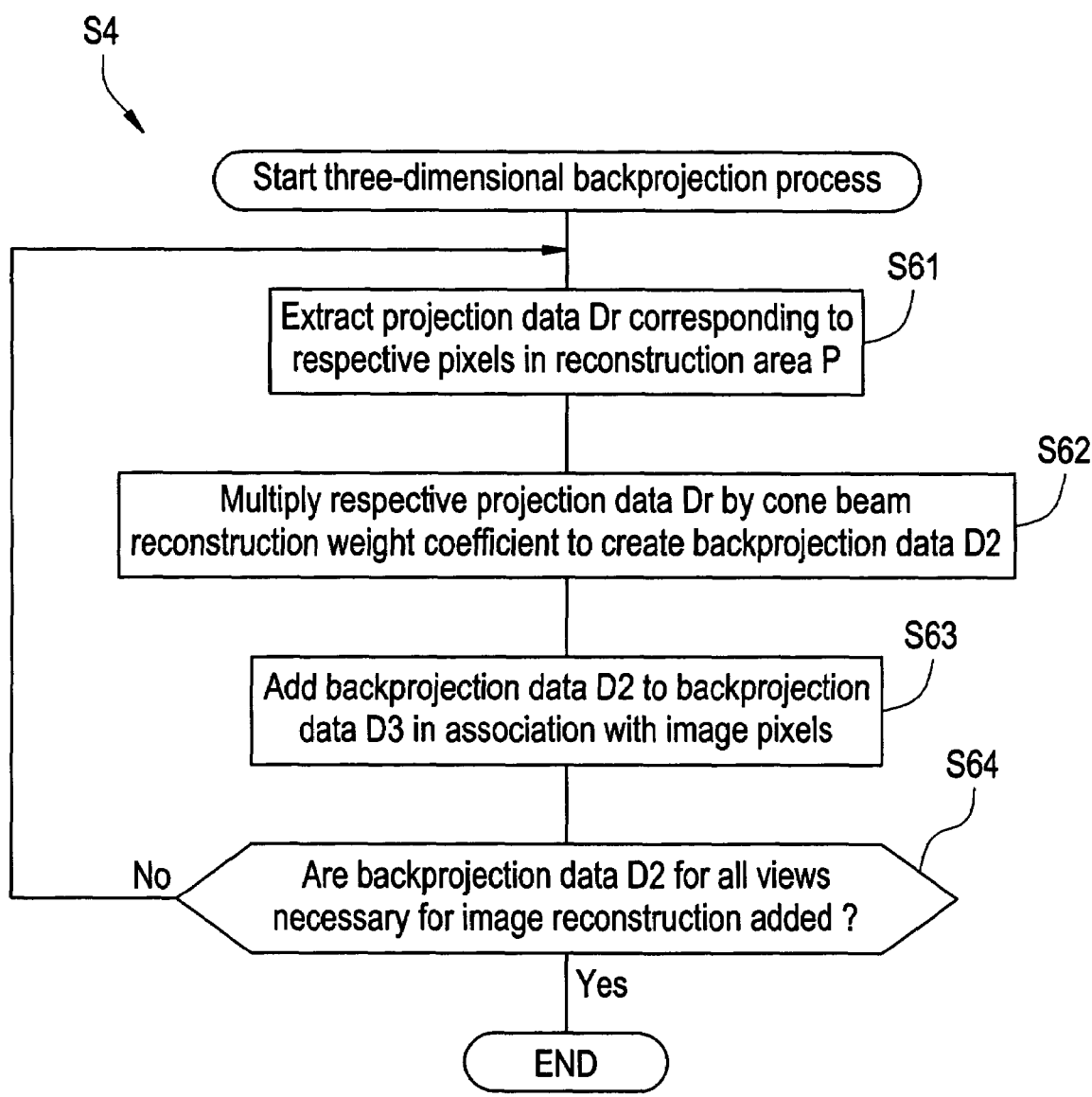
FIG. 22 is a flow diagram illustrating the details of a three-dimensional image reconstructing process.

FIG. 22 is a flow diagram showing the details of the three-dimensional backprojection process (Step S4 in FIG. 3). In Step S61, attention is paid to one of all views (i.e., views corresponding to 360° or views corresponding to "180°+fan angles") necessary for reconstruction of a CT image. Projection data Dr corresponding to respective pixels in a reconstruction area P are extracted.

Figure 23A:
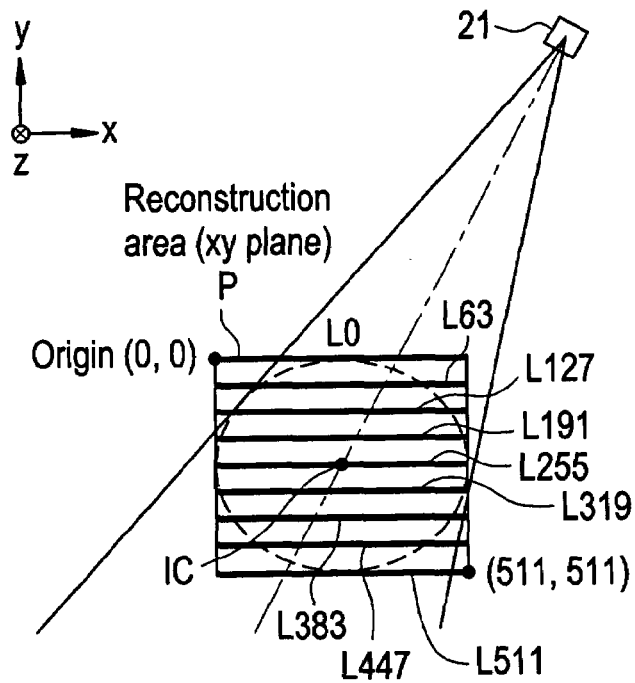
FIGS. 23a and 23b are conceptual diagrams showing a state in which lines on a reconstruction area are projected in an X-ray penetration direction.
Figure 23B:
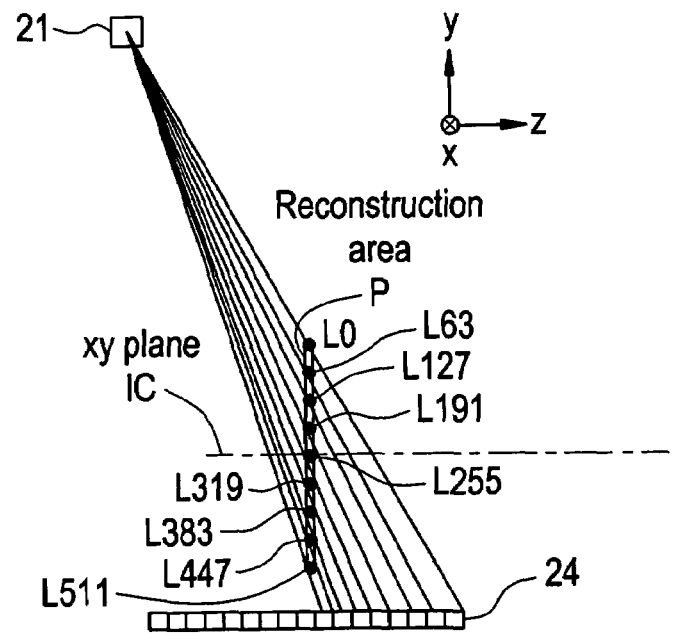
Figure 24:
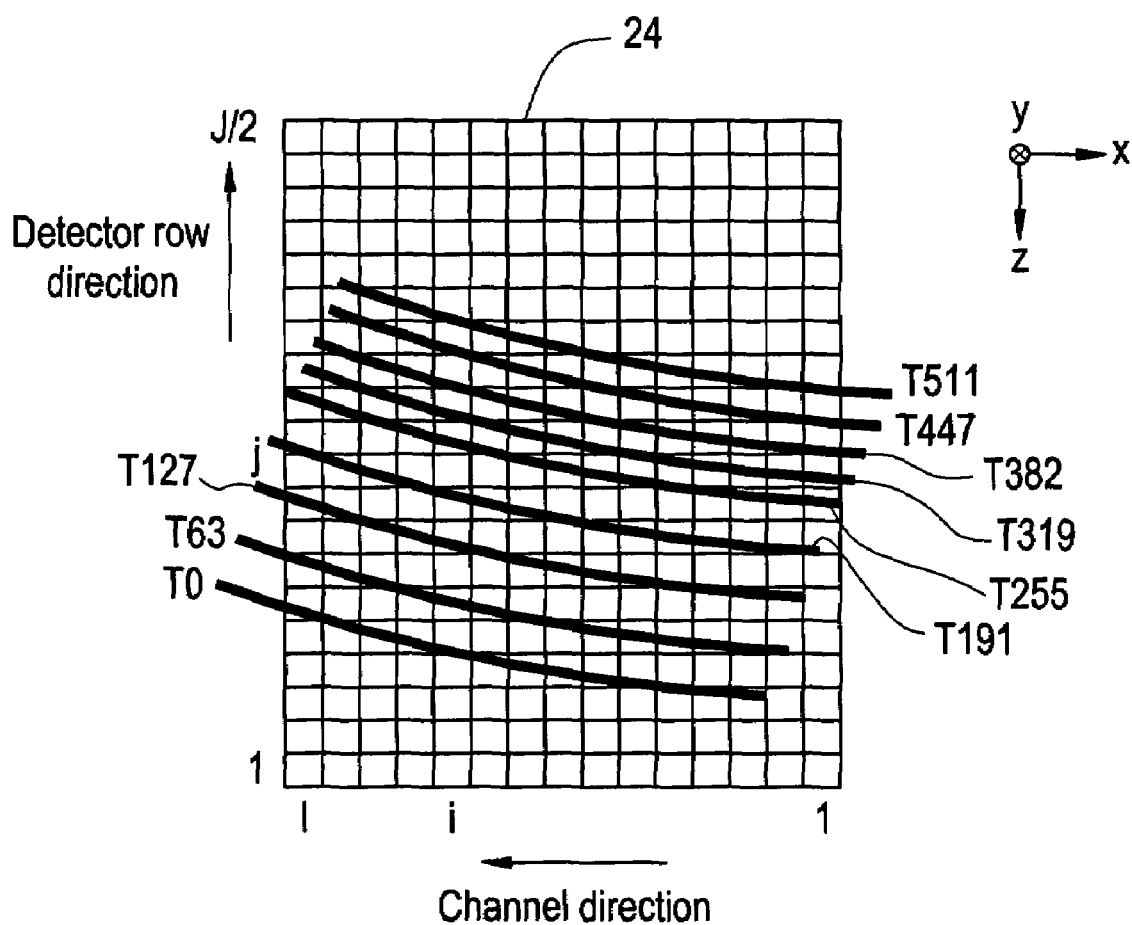
FIG. 24 is a conceptual diagram depicting lines projected on a detector plane.

As shown in FIG. 23, a square area of 512×512 pixels, which is parallel to an xy plane, is defined as a reconstruction area P, and a pixel row L0 parallel to an x axis of y=0, a pixel row L63 of y=63, a pixel row L127 of y=127, a pixel row L191 of y=191, a pixel row L255 of y=255, a pixel row L319 of y=319, a pixel row L383 of y=383, a pixel row L447 of y=477, and a pixel row L511 of y=511 are taken as rows respectively. In this case, when projection data on lines T0 through T511 shown in FIG. 24 obtained by projecting these pixel rows L0 through L511 on the plane of the multi-row X-ray detector 24 in an X-ray penetration direction are extracted in such a condition, then they result in projection data Dr for the pixel rows L0 through L511.

Although the X-ray penetration direction is determined depending on geometrical positions of an X-ray focal point of the X-ray tube 21, the respective pixels and the multi-row X-ray detector 24. Since, however, the z coordinates of projection data D0 (z, view, j, i) are known, the X-ray penetration direction can be accurately determined even in the case of the projection data (z, view, j, i) placed under acceleration and deceleration.

Incidentally, when some of lined are placed out of the plane of the multi-row X-ray detector 24 as in the case of, for example, the line T0 obtained by projecting the pixel row L0 on the plane of the multi-row X-ray detector 24 in the X-ray penetration direction, the corresponding projection data Dr is set to "0".

Figure 25:
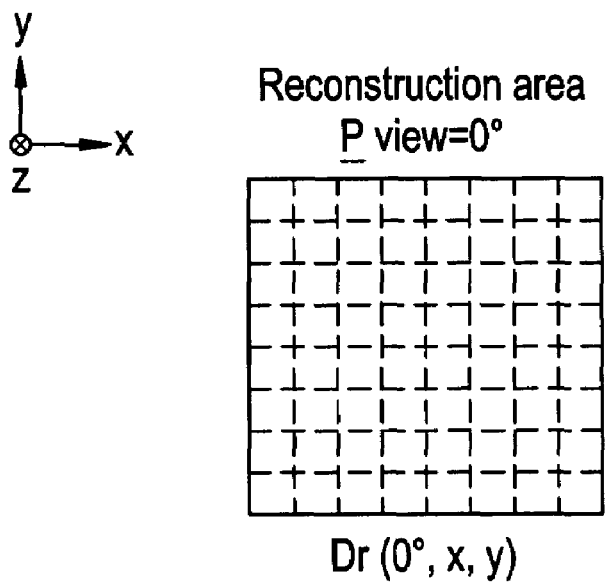
FIG. 25 is a conceptual diagram illustrating a state in which projection data Dr (view, x, y) are projected on a reconstruction area.

Thus, as shown in FIG. 25, the projection data Dr (view, x, y) corresponding to the respective pixels of the reconstruction area P can be extracted.

Figure 26:
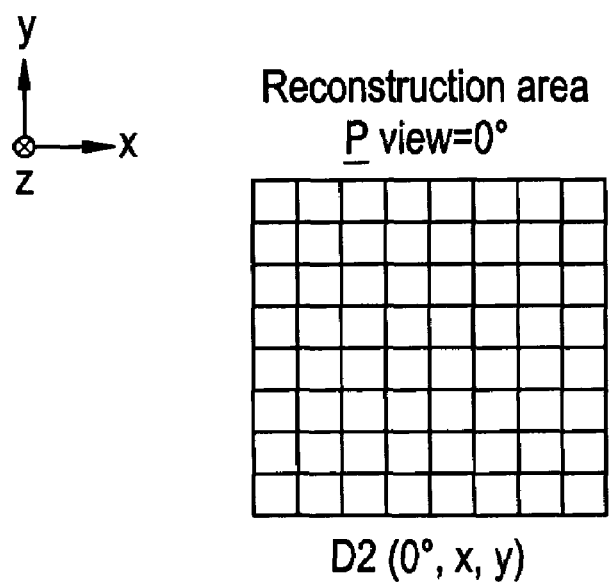
FIG. 26 is a conceptual diagram showing backprojection pixel data D2 of respective pixels on a reconstruction area.

Referring back to FIG. 22, in Step S62, the projection data Dr (view, x, y) are multiplied by a cone beam reconstruction weight coefficient to create projection data D2 (view, x, y) shown in FIG. 26.

When the distance between the focal point of the X-ray tube 21 and each of a detector row j of the multi-row detector 24, corresponding to the projection data Dr and a channel i thereof is assumed to be r0, and the distance between the focal point of the X-ray tube 21 and each of the pixels on the reconstruction area P corresponding to the projection data Dr is assumed to be r1 here, the cone beam reconstruction weight coefficient becomes $(r1/r0)^2$.

In Step S63, as shown in FIG. 27, the projection data D2 (view, x, y) are added to the backprojection data D3 (x, y) cleared in advance, in association with pixels.

In Step S64, Steps S61 through S63 are repeatedly effected on all views (i.e., views of 360° or views of "180°+fan angles") necessary for reconstruction of a CT image to obtain backprojection data D3 (x, y) as shown in FIG. 27.

Incidentally, the reconstruction area P may be configured as a circular area as shown in FIG. 28.

According to the X-ray CT apparatus 100 described above, projections data are acquired or collected even during not only a period in which a table linear movement velocity is being kept constant but also a period in which a table linear movement is being under acceleration/deceleration. Coordinate information in a body-axis direction (hereinafter called z axis) while the scan is running, is added to each view data or several view data once. The acquired projection data are used for image reconstruction together with z-axis coordinates and information. Therefore, a table linear moving distance for acceleration/deceleration, of the entire table linear moving distance is also available for image reconstruction.

Incidentally, the image reconstructing method may be the two-dimensional image reconstructing method known to date or a three-dimensional image reconstructing method based on the FeldKamp method known to date. Further, three-dimensional image reconstructing methods proposed by Japanese Patent Application Nos. 2002-066420, 2002-147061, 2002-147231, 2002-235561, 2002-235662, 2002-267833, 2002-322756 and 2002-338947 may be used.

Many widely different embodiments of the invention may be configured without departing from the spirit and the scope of the present invention. It should be understood that the present invention is not limited to the specific embodiments described in the specification, except as defined in the appended claims.

The invention claimed is:

1. A collimator control method for an X-ray CT apparatus wherein a subject is helically scanned in a direction of a body axis thereof using an X-ray beam formed by a collimator, and image reconstruction is performed based on projection data obtained through an X-ray detector, said method comprising:
   changing an aperture of the collimator according to a position of a helical scan on the body axis of the subject in the process of progress of the helical scan, said changing comprising:
   opening the aperture during an acceleration of the progress of the helical scan in the body-axis direction; and
   closing the aperture during a deceleration of the progress of the helical scan in the body-axis direction.

2. The collimator control method according to claim 1, wherein the acceleration and the deceleration of the progress of the helical scan in the body-axis direction are linear.

3. The collimator control method according to claim 1, wherein the acceleration and the deceleration of the progress of the helical scan in the body-axis direction are nonlinear.

4. The collimator control method according to claim 1, wherein said position of a helical scan on the body axis of the subject in the process of progress of the helical scan is based on a coordinate of the body axis direction which is measured during the helical scan.

5. The collimator control method according to claim 1, wherein the aperture defines a predetermined opening, a first half of the predetermined opening extending from a center point of the aperture forward along the body axis to a front edge of the aperture and a second half of the predetermined opening extending from the center point of the aperture backwards along the body axis to a back edge of the aperture, said changing comprising:
   at a start position of the helical scan, opening the first half and closing the second half such that the aperture is at about one-half of the predetermined opening at the first half;
   at an intermediate position of the helical scan in the direction of the progress of the helical scan, opening the aperture to the predetermined opening by opening the first half and the second half; and
   at an end position of the helical scan, closing the aperture at the first half such that the aperture is opened by about one-half of the predetermined opening at the second half.

6. The collimator control method according to claim 1, wherein said changing comprises changing the aperture continuously during the helical scan.

7. An X-ray CT apparatus comprising:
   an X-ray source;
   a collimator for shaping X-rays emitted from the X-ray source;
   a control device for controlling the collimator;
   an X-ray detector disposed so as to be opposed to the X-ray source and the collimator with a subject interposed therebetween; and
   an image reconstructing device for helically scanning the subject in a direction of a body axis thereof and reconstructing an image on the basis of projection data obtained through the X-ray detector,
   wherein the control device changes an opening degree of an aperture of the collimator according to a position of a helical scan on the body axis in the process of progress of the helical scan, said control device configured to:
      open the aperture during an acceleration of the progress of the helical scan in the body-axis direction; and
      close the aperture during a deceleration of the progress of the helical scan in the body-axis direction.

8. The X-ray CT apparatus according to claim 7, wherein the acceleration and the deceleration of the progress of the helical scan in the body-axis direction are linear.

9. The X-ray CT apparatus according to claim 7, wherein the acceleration and the deceleration of the progress of the helical scan in the body-axis direction are nonlinear.

10. The X-ray CT apparatus according to claim 7, wherein said position of a helical scan on the body axis of the subject in the process of progress of the helical scan is based on a coordinate of the body axis direction which is measured during the helical scan.

11. The X-ray CT apparatus according to claim 7, wherein the aperture defines a predetermined opening, a first half of the predetermined opening extending from a center point of the aperture forward along the body axis to a front edge of the aperture and a second half of the predetermined opening extending from the center point of the aperture backwards along the body axis to a back edge of the aperture, said control device configured to:
   at a start position of the helical scan, open the first half and close the second half such that the aperture is at about one-half of the predetermined opening at the first half;
   at an intermediate position of the helical scan in the direction of the progress of the helical scan, open the aperture to the predetermined opening by opening the first half and the second half; and
   at an end position of the helical scan, close the aperture at the first half such that the aperture is opened by about one-half of the predetermined opening at the second half.

12. The X-ray CT apparatus according to claim 7, wherein said control device is further configured to change the aperture continuously during the helical scan.

* * * * *